United States Patent
Sharma et al.

(10) Patent No.: US 6,682,884 B2
(45) Date of Patent: Jan. 27, 2004

(54) METHOD AND DEVICE FOR THE RAPID CLINICAL DIAGNOSIS OF HEPATITIS B VIRUS (HBV) INFECTION IN BIOLOGICAL SAMPLES

(76) Inventors: Vijay Sharma, Flat 197, 19th Floor, Naperol Towers, B Wing, R.A. Kidwai Marg, Wadala, Mumbai 400 131 (IN); Venkata Ramana Kondiboyina, 307, Sahyadri, Neelakanth Valley, Ghatkopar (E), Mumbai 400 077 (IN)

( * ) Notice: Subject to any disclaimer, the term of this patent is extended or adjusted under 35 U.S.C. 154(b) by 0 days.

(21) Appl. No.: 10/037,884

(22) Filed: Jan. 3, 2002

(65) Prior Publication Data

US 2003/0157478 A1 Aug. 21, 2003

(51) Int. Cl.[7] .............................. C12Q 1/70; C12Q 1/68
(52) U.S. Cl. ................................ 435/5; 435/6; 536/24.3; 536/24.32; 536/24.33
(58) Field of Search ..................... 435/5, 6; 536/24.3, 536/24.32, 24.33

(56) References Cited

FOREIGN PATENT DOCUMENTS

| EP | 0569237 A2 | * | 11/1993 |
| JP | 11262399 A | * | 9/1999 |

* cited by examiner

Primary Examiner—Donna C. Wortman
(74) Attorney, Agent, or Firm—J. Harold Nissen; Lackenbach Siegel LLP

(57) ABSTRACT

There is provided a method and kit for rapid clinical diagnosis of HBV in which the amplimers are transcripts of a pre-core or envelop region gene of HBV. The amplicons are hybridized to a specific oligonucleotide probe, which allows the amplicons to be detected.

22 Claims, No Drawings

METHOD AND DEVICE FOR THE RAPID CLINICAL DIAGNOSIS OF HEPATITIS B VIRUS (HBV) INFECTION IN BIOLOGICAL SAMPLES

BACKGROUND OF THE INVENTION

1. Field of Invention

The present invention relates to methods and devices for the diagnosis of infections. In particular, the present invention relates to methods and kits for detection of *Hepatitis B Virus* Viremia (HBV).

2. Description of the Prior Art

*Hepatitis B* virus (HBV) is an enveloped hepatotropic DNA virus. Acute and chronic HBV infection causes significant liver diseases and it is estimated that more than 300 million individuals world wide are chronically infected with HBV. The HBV genome is unique in the world of viruses due to its compact nature, use of overlapping reading frames, and dependence on a reverse-transcriptional step, though the virion contains primarily DNA. The human *hepatitis B* virus is a member of the *Hepadna Viridae* family which includes duck hepatitis virus (DHBV), Ground squirrel hepatitis virus (GSHV), snow goose *hepatitis B* virus (sgHBV), woodchuck hepatitis virus (WHV) and wooly monkey hepatitis virus.

Furthermore, persistent viral infection leads to chronic active hepatitis, liver cirrhosis and the development of *hepatocellular carcinoma*. It has recently been appreciated that individuals who recover from HBV infection have a broad based cellular immune response to HBV structural proteins. Indeed, cytotoxic lymphocyte activity (CTL) may be critical for promoting viral clearance from the liver and CTL activity has been detected many years after resolution of acute infection. The presence of CTL activity may be due to persistence of low level HBV infection in the liver that can be identified only by molecular techniques such as PCR. Thus, the concept has arisen that even if individuals serologically recover from HBV infection, the virus, in most instances is never completely irradicated from the liver. *Hepatitis B* is of great medical importance because *Hepatocellular carcinomas*(HCC), one of the most common cancers afflicting humans, is primarily caused by chronic HBV infection. In the last few decades, the correlation between HBV and the development of HCC has been well established. However, the mechanism by which HBV transforms hepatocytes remains elusive. It is noticed that before HBV can transform a cell, the virus first infects it. However, the mechanism through which HBV enters hepatocyte has not been resolved despite further understanding of the viral protein involved. Much more research is needed before it is fully understood by the scientist and the spread of this infectious agent is controlled.

It is noticed that in individuals who become persistently infected with HBV is due to lack of a broad based cellular immune response for unclear reasons. In this context, there are often deletions and mutations within the envelope and core genes that may allow for persistent viral infection to occur. Alternatively, these mutant viral strains may evolve as the result of immune selection pressure by the host. In specific instances, mutations in the viral genome can lead to or contribute to the generation of latent viral infection. Furthermore, specific mutations in the precore region that includes the regulatory elements may lead to more severe disease such as fulminant hepatitis.

Cellular and humoral immune responses to HBV antigens are believed to play an essential role in the elimination of virus by the infected host. The activity of a broad-based cellular immune response to different HBV antigens has been demonstrated to be one of the most important factors contributing to virus clearance from infected hepatocytes. One hypothesis to explain the development of persistent viral infection is that HBV-specific CTLs are unable to clear virus from the liver because of substantially decreased intrahepatic levels or qualitative changes in CTL activity. Cellular immune responses against HBV may therefore play an important role in the pathogenesis of viral hepatitis as well as determine the development, severity and outcome of chronic liver disease. The cellular immune response to HBV is strong and multispecific in acutely infected patients, and these T lymphocytes typically secrete TH1-like antiviral cytokines such as interferon-a (IFN-a) and tumor necrosis factor-a (TNF-a) upon antigen stimulation. In contrast, the cellular immune response in patients persistently infected with HBV is weak and narrowly focused.

However, it is known that some chronically infected individuals spontaneously clear HBV from serum, and this phenomenon is often accompanied by increased CD4+ T lymphocyte responses and acute exacerbation of liver disease as manifested by increased serum alanine aminotransferase levels. The observation of spontaneous HBV clearance in some patients implies that the suboptimal cellular immune response may be reversible. Therefore, strategies to enhance the HBV-specific immune response or to alter the balance between certain components of the response may be able to terminate persistent infection.

Early and rapid diagnosis of HBV infection is of great importance. Yet, conventional methods for detection of HBV from serum, plasma are inaccurate and/or slow. Serologic markers are commonly used as diagnostic and/or prognostic indicators of acute or chronic HBV infection. The most common marker of HBV infection is the presence of HBV surface antigen (HBs Ag). Although carriers may clear HBs Ag and develop antibody to HBs Ag, there appears to still be a risk of serious liver complications later in life. HBs Ag is generally used as a secondary marker to indicate active HBV replication associated with progressive live disease. Failure to clear HBs Ag appears to increase the risk of end stage liver disease.

Various strains of HBV can either produce HBs Ag that is not detectable in serum or the strain can lose the ability to make HBs Ag even when an active infection is present. The ability to detect HBV DNA in serum has been reported to have prognostic value for the outcome of acute and chronic HBV infections. The methodology can allow the detection of HBV DNA after HBs Ag clearance or detection of HBV lacking serologic makers.

The following requirements need to be fulfilled for an optimal assay for HBV diagnosis.

High sensitivity and specificity;

Rapid results; and

High reproducibility.

Kits for detection of HBV are commercially available. One such kit is produced by Hoffmann-La Roche and sold under the tradename Amplicor. This kit makes use of amplification by Polymerase Chain Reaction (PCR) to create amplicons specific to HBV followed by Enzyme Linked Immunosorbent Assay (ELISA) to detect the amplicons. Furthermore, the test is an in vitro amplification test for the quantification of *Hepatitis B* Viral DNA in human serum or plasma. The test is not intended for use in screening blood or blood products for the presence of *Hepatitis B* Virus.

In light of the foregoing, there is a need for a more sensitive and specific detection protocol for clinical samples.

The inventors of the present invention have been successful in developing a kit and a method for detecting HBV in a more sensitive, specific and rapid manner. The present invention obviates the problems associated with the conventional kits.

Several terms used in the invention are defined as follows.

The term "primer" refers to a synthetic oligonucleotide sequence synthesized for annealing to a specific nucleotide sequence of interest. The primer initiates DNA synthesis to occur using thermostable DNA dependent DNA polymerase. Selecting the proper primer is one of the most important steps in designing a PCR kit. The primer set must hybridize to the target sequence with little or no hybridization to other sequences that are also present in the sample.

The term "probe" refers to a synthetic oligonucleotide sequence which lies internal to the + strand of the amplified product resulting from a PCR reaction.

The term "hybridization" refers to annealing of nucleotide sequences to each other under optimal conditions. Typically, a nucleotide A binds to nucleotide T and nucleotide G binds to nucleotide C.

The term "biological samples" refers to the samples selected from serum, plasma, whole blood, urine, paraffin embedded tissue, and combinations thereof. When selected, plasma and whole blood samples will preferably include an anticoagulant, such as EDTA and/or ACD.

SUMMARY OF THE INVENTION

It is an object of the present invention to develop an improved HBV diagnostic kit.

It is an object of the present invention to develop an improved method for rapid clinical diagnosis of HBV infection.

It is still an object of the invention is to develop a method using specific primer sets and detection probe having higher sensitivity and specificity as compared to the conventional assays.

These and other objects of the present invention are substantially achieved by a method and kit for rapid clinical diagnosis of HBV in which the amplimers are transcripts of a pre-core or envelop region gene of HBV. The amplicons are hybridized to a specific oligonucleotide probe, which allows the amplicons to be detected.

DESCRIPTION OF THE INVENTION

Selecting the target DNA sequence, Polymerase gene large envelop core protein (Sgene) for HBV depends upon identification of regions within the HBV genome that show maximum sequence conservation among all the serotypes of HBV.

The present invention has primers complementary to sequences flanking a segment of the Polymerase gene large envelop core protein (Sgene) to be amplified. The primers of the present invention are selected on their ability to specifically recognize the Polymerase gene large envelop core protein (Sgene) with a low mutation frequency.

The primers of the present invention are so designed to avoid hairpin loop structure formation. In addition, the selected primers have been subjected to a gene bank search to identify homologies and percent similarities to the target of interest. The blast search results are as follows:

For SEQ. ID. NO. 1, SEQ. ID. NO. 2 and SEQ. ID. NO. 3, the accession No: NC-001707 yielded 100% homology A diagnostic kit for detection of HBV in biological samples according to the present invention includes two components. The first component is the amplification component, which is used to amplify the target sequence. The second component of the kit is the detection component, which is used to detect the amplicons produced by the amplification component.

The amplification component amplifies the target sequence via PCR and, therefore, will include a pair of amplification oligonucleotide primers, a DNA-dependent DNA polymerase; and deoxyribonucleoside triphosphates. The primers are labeled at their 5' end. Labels are preferably selected from the group consisting of fluorescein, biotin, digoxigenin, and radioactive labels (e.g., $^{32}P$). A more preferable label is fluorescein.

The first oligonucleotide primer for use in the amplification component has the following nucleic acid sequence (SEQ. ID. NO. 1):

5'-atactgcggaactcctagc-3'

SEQ. ID. NO. 1 contains nineteen (19) continuous bases selected from the pre-core or envelop region sense strand. The Nucleotide Sequence position of SEQ. ID. NO. 1 is 1142–1160. SEQ. ID. NO. 1 is preferably present in the amplification component in an amount of about 1 $\mu$L to about 10 $\mu$L in a concentration of 10–100 pM.

The second oligonucleotide primer for use in the amplification component has the following nucleic acid sequence (SEQ. ID. NO. 2):

5'-gttcacggtggtctccatgcgacgtgc-3'

SEQ. ID. NO. 2 contains twenty seven (27) continuous bases selected from the pre-core or envelop region antisense strand. The Nucleotide Sequence position of SEQ. ID. NO. 2 is 1499–1473. SEQ. ID. NO. 2 is preferably present in the amplification component in an amount of about 1 $\mu$L to about 10 $\mu$L in a concentration of 10–100 pM.

The annealing temperature of primer pair is generally calculated as 5° C. lower than the estimated melting temperature. The annealing temperature for primers that are less than 20 bases is calculated using the following formula: [4(G+C)+2(A+T)]−5° C. Ideally the annealing temperature of each primer should match and be within the 55° C. and 75° C. range. If the annealing temperature difference between the two primers is high, the lower annealing temperature can be increased adding to the length of that primer at either the 3' end (this can also keep the size of the amplified locus constant) or the 5' end. The annealing temperature for the primers of the present invention is about 68° C.

The thermostable DNA-dependent DNA polymerase may be any suitable polymerase. Preferably, the polymerase is derived from *Thermus aquaticus* (Taq) bacteria. The polymerase is preferably present in the amplification component in an amount of about 1 Unit to about 2.5 Units.

The deoxyribonucleoside triphosphates (dNTPs) useful in the present invention include: dATP, dCTP, 5MedCTP, dGTP, dITP, TTP, and dUTP. Preferably, the dNTPs are selected from dATP, dCTP, dGTP, dTTP, and combinations thereof. Preferably, each dNTP is present in the amplification component in an amount of about 100 $\mu$M to about 200 $\mu$M.

The amplification component may contain any other suitable additional ingredient and/or component, such as an amplification buffer. For example, suitable 10× amplification buffers for use in the present invention include 100 mM Tris HCl (pH 8.3), 500 mM KCl, and $MgCl_2$.

A preferred amplification component includes:
(1) an amplification buffer having 10 mM Tris HCl (pH 8.3) and 500 mM KCl;
(2) about 100 to about 200 $\mu$M each of dATP, dCTP, dTTP and dGTP;

(3) sterile distilled water(nuclease free);
(4) about 1 unit to about 2.5 units of thermostable DNA-dependent DNA polymerase;
(5) about 10 to about 100 pM of the first oligonucleotide primer (SEQ. ID. NO. 1);
(6) about 10 to about 100 pM of the second oligonucleotide primer (SEQ. ID. NO. 2);
(7) about 1.5 to about 2.5 mM $MgCl_2$; and
(8) the template to be amplified.

Preferably, the volume of the amplification buffer is about 25 to about 50 µL and the volume of the extracted sample is about 25 to about 50 µL. The final volume of the amplification component is about 50 to about 100 µL.

The detection component detects the amplified target sequence via ELISA and, therefore, will include a oligonucleotide probe immobilized upon a solid medium, a conjugate that is adapted to bind to a label present on the amplicons, and a complex that changes color in the presence of the conjugate.

The oligonucleotide probe has the following a nucleic acid sequence (SEQ. ID. NO. 3):

5'-gggcgcacctctctttacgcgg-3'

The Nucleotide Sequence position of SEQ. ID. NO. 3 is 1396–1417 and contains twenty two (22) continuous bases. SEQ. ID. NO. 3 is a region internal to the amplimers created using the primers of SEQ. ID. NO. 1 and SEQ. ID. NO. 2

SEQ. ID. NO. 3 is specifically designed for capturing the amplification product. The oligonucleotide probe is preferably immobilized on a solid medium, such as a microwell plate. For example, the oligonucleotide probe is labeled at their 5' end with biotin, which is substantially irreversibly bound to streptavidin coating the microwell plate.

The oligonucleotide probe is preferably present in the detection component in an amount of about 10 µL to about 100 µL in a concentration of 10–100 pM.

Since the label on the amplicon is preferably fluorescein, the conjugate is preferably an anti-fluorescein/horseradish peroxidase (HRP) conjugate present in an amount of about 1 unit to about 4 units. However, any suitable conjugate may be used, depending only upon the label present on the amplicon.

The enzyme on the conjugate may be any enzyme, depending only upon the selected substrate. For example, the preferred enzyme for the present invention is horseradish peroxidase (HRP). However, other enzymes such as and alkaline phosphatase may be used.

The substrate changes color in the presence of the enzyme conjugate to visibly show the presence of the amplimer bound to the oligonucleotide probe. Thus, a change in the color of the detection solution positively indicates the presence of the amplimer and, by extension, the presence of HBV in the original biological sample. The selection of the substrate is dependent upon the selected enzyme on the conjugate. A preferred enzyme and substrate combination for use in the present invention is peroxidase and a mixture of hydrogen peroxide ($H_2O_2$) and 3,3',5,5'-Tetra methybenzidine hydrochloride(TMB), present in an amount of about 100 µL, which is oxidized by $H_2O_2$ in the presence of peroxidase and, thus, the detection solution changes from colorless to blue. Other suitable enzyme and substrate combinations are as follows:

Alkaline Phosphatase and 5-Bromo-4Chloro-3Indolyl Phosphate (BCIP)
Alkaline Phosphatase and Fast Red RC
Alkaline Phosphatase and Naphthol AS-TR Phosphate
Alkaline Phosphatase and Nitro Blue Tetrazolium (NBT)
Alkaline Phosphatase and p-Nitrophenyl Phosphate (pNPP)
Peroxidase and 3-Amino-9-Ethylcarbazole (AEC)
Peroxidase and 5-Aminosalicyclic acid (5AS)
Peroxidase and 2,2'-Azino-bis(3-Ethylbenzthiazoline-6-Sulfonic acid)
Peroxidase and 4-Chloro-1-Naphthol (4ClN)
Peroxidase and 3–3'Diaminobenzidine Tetrahydrochloride (DAB)
Peroxidase and o-Dianisidine
Peroxidase and o-Phenylenediamine Freebase (OPD)

A method for rapid clinical diagnosis HBV according to the present invention uses the first primer (SEQ. ID. NO. 1) and the second primer (SEQ. ID. NO. 2) in an amplification step, and the oligonucleotide probe (SEQ. ID. NO. 3) in a detection step.

In accordance with a second aspect of this invention, a method according to the present invention includes the steps of sample extraction, amplification (preferably by PCR), and detection by enzyme immunoassay (preferably ELISA).

HBV nucleic acid is extracted from a biological sample, preferably using chaotropic agents such as urea, diethylamine, guanidium hydrochloride, potassium iodide, sodium dodecyl sulphate (SDS), Formamide, and combinations thereof. Any suitable and/or known technique for extraction of nucleic acid may be used.

The extracted specimen is then added to an amplification component. As discussed above, the amplification component contains the primers of the present invention (SEQ. ID. NOs. 1 and 2), having a label at their 5' ends, deoxyribonucleoside triphosphates, and a thermostable DNA dependent DNA polymerase.

Amplification is accomplished by repeated cycles of: DNA denaturation, primer annealing, and extension of the primed DNA sequence by the DNA polymerase in the presence of added purine and pyrimidine bases. In general, each cycle will double the amount of the target DNA sequence. The amplification cycle is repeated until a detectable amount of the DNA sequence has been created. Further details of the PCR method are provided in U.S. Pat. Nos. 4,683,195; 4,683,202; 4,965,188; and 5,075,216, which are incorporated herein by reference in their entirety.

The amplimers are preferably detected using ELISA. Denatured and labeled amplimers are added to a microwell containing the immobilized oligonucleotide probe of the present invention (SEQ. ID. NO. 3) and a hybridization solution, thereby immobilizing the amplimers by hybridization with the oligonucleotide probe. An anti-fluorescein conjugate with a selected enzyme is added to the microwell after excess unbound amplimers are washed away. Finally, a substrate is added to the microwell, which changes color in the presence of the anti-fluorescein conjugate. Thus, the detection solution changes color if any amplimers are present in the microwell, which denotes a positive result for the presence of HBV in the original biological sample.

This method is rapid, automatable (ELISA type solid phase formats do not require gel electrophoresis) and applicable to large scale screening programs.

The following example illustrates the process according to the invention without limitation.

EXAMPLE 1

An experiment was conducted to demonstrate the method of present invention. The initial sample taken was plasma EDTA that was pre-determined as positive for the presence of HBV mediated antibodies (IgG, IgM) and *Hepatitis B*

Surface Antigen (HbSAg). The sample (0.2 ml) was extracted using the a DNA isolation system sold by Qiagen Inc., Venlo, The Netherlands, under the tradename QIAamp®.

The amplification reaction was set up using 25 μL of the above extracted nucleic acid and 25 μL of 10× amplification buffer including 100 mM Tris HCl (pH 8.3), 500 mM KCl, and $MgCl_2$ was added to make a final concentration of about 1.5 mM to about 2.5 mM. The primers (SEQ. ID. NOs. 1 and 2) were labeled with fluorescein and provided in a concentration of about 10 pM. Each dNTP (dATP, dCTP, dGTP, and dTTP) was provided in a concentration of 100–200 μM. Taq polymerase was provided in an amount of about 1–2.5 units.

This reaction mixture was heated to 94° C. for 10 min followed by 30 cycles. Each cycle comprises of 94° C. for 30 sec, 62° C. for 45 sec, and 72° C. for 30 sec. Following the 30 cycles, the final incubation was performed for 10 min at 72° C. The resulting amplimers were denatured using a solution of 0.4 M NaOH.

The detection of the fluorescein labeled amplimers was done in the following manner:

50–100 μL of dilution buffer was pipetted into a microwell plate coated with streptavidin, to which was added 1–10 μL of the biotinylated oligonucleotide probe (SEQ. ID. NO. 3). The solution was incubated at 37° C. for 30–60 min. Thereafter, the microwell plate was washed with PBS-T wash buffer, and 100 μL of the hybridization buffer was added and incubated for 15–30 min at 37° C. The hybridization buffer included sodium phosphate, sodium thiocyanade and Denhardts solution which included Polyvinylpyrrolidine (PVP), Ficoll, Bovine Serum Albumin (BSA)]

25 μL of denatured amplification product was added to the microwell plate and incubated for 30–60 min at 42° C. Following incubation, the microwell plate was washed 5 times with PBS-T wash buffer. 100 μL of diluted anti-fluorescein-HRP conjugate was added to the washed plate and incubated for 30–45 min at 37° C. Following incubation, the microwell plate was washed 5 times with PBS. 100 μL of TMB was added to the microwell plate and incubated substantially without light at room temperature for 15–30 minutes.

A color change from colorless to blue is observed after incubating for 15 min. 50 μL of a stop solution containing 0.1 N $H_2SO_4$ was added and the change in color from blue to yellow was noticed and the plate was read at 403 nm in a calorimetric plate reader, and read at 403 nm.

In view of the foregoing descriptions and example, it will become apparent to those of ordinary skill in the art that equivalent modifications thereof may be made without departing from the spirit and scope of this invention. Various features are set forth in the following claims.

We claim:

1. A kit for amplifying HBV Polymerase nucleic acid comprising:
   a sense amplification primer consisting of the sequence:
   5'-atactgcggaactcctagc-3'[SEQ. ID. NO. 1]
   and an anti-sense amplification primer consisting of the sequence:
   5'-gttcacggtggtctccatgcgacgtgc-3'[SEQ. ID. NO. 2]

2. The kit according to claim 1, wherein the sense amplification primer is present in a concentration of about 10 to about 100 pM.

3. The kit according to claim 1, wherein the anti-sense amplification primer is present in a concentration of about 10 to about 100 pM.

4. The kit according to claim 1, further comprising thermostable DNA dependent DNA polymerase.

5. The kit according to claim 4, wherein the DNA polymerase is Taq polymerase present in an amount of about 1 Unit to about 2.5 Units.

6. The kit according to claim 1, further comprising a deoxyribonucleoside triphosphate.

7. The kit according to claim 6, wherein said deoxyribonucleoside triphosphate is selected from the group consisting of: dATP, dCTP, 5MedCTP, dGTP, dITP, TTP, dUTP, and combinations thereof.

8. The kit according to claim 6, wherein said deoxyribonucleoside triphosphate is present in a concentration of about 100 to about 200 $\mu$M.

9. The kit according to claim 1, wherein the sense and anti-sense amplification primers have a label at their respective 5' ends.

10. The kit according to claim 9, wherein the label is fluorescein.

11. A method for detecting HBV Polymerase nucleic acid in a biological sample comprising the steps of:
extracting HBV nucleic acid from a biological sample;
amplifying HBV Polymerase nucleic acid using a sense primer consisting of the sequence
5'-atactgcggaactcctagc-3'[SEQ. ID. NO. 1]
and a anti-sense primer consisting of the sequence
5'-gttcacggtggtctccatgcgacgtgc-3'[SEQ. ID. NO. 2]
and detecting the HBV Polymerase nucleic acid using an oligonucleotide probe consisting of the sequence:
5'-gggcgcacctctctttacgcgg-3'[SEQ. ID. NO. 3].

12. The method according to claim 11, wherein the biological sample is selected from the group consisting of serum, plasma, whole blood , urine, paraffin embedded tissue, and combinations thereof.

13. The method according to claim 11, wherein the sense and anti-sense amplification primers have a label at their respective 5' ends.

14. The method according to claim 13, wherein the label is fluorescein.

15. The method according to claim 11, wherein amplifying the HBV nucleic acid comprises the steps of:
denaturing the HBV nucleic acid to produce denatured HBV nucleic acid;
annealing the sense and anti-sense amplification primers to the denatured HBV nucleic acid to produce primed HBV nucleic acid; and
extending the primed HBV nucleic acid using a thermostable DNA dependent DNA polymerase in the presence of a deoxyribonucleoside triphosphate.

16. The method according to claim 15, wherein the DNA dependent DNA polymerase is Taq polymerase present in an amount of about 1 Unit to about 2.5 Units.

17. The method according to claim 15, wherein the deoxyribonucleoside triphosphate is selected from the group consisting of: dATP, dCTP, 5MedCTP, dGTP, dITP, TTP, dUTP, and combinations thereof, and wherein the deoxytibonucleoside triphosphate is present in a concentration of about 100 to about 200 $\mu$M.

18. The method according to claim 11, wherein detecting the HBV nucleic acid comprises of:
binding the HBV nucleic acid with the oligonucleotide probe attached to a solid medium to form immobilized HBV nucleic acid;
binding the immobilized HSV nucleic acid with a conjugate; and
adding a substrate that is adapted to change color in the presence of an enzyme on the conjugate,
whereby a change of the color of the substrate indicates the presence of HBV nucleic acid.

19. The method according to claim 18, wherein the HBV nucleic acid is labeled with fluorescein, and wherein the conjugate is an anti-fluorescein/horseradish peroxidase (HRP) conjugate in an amount of about 1 unit to about 4 units.

20. The method according to claim 18, wherein the substrate comprises hydrogen peroxide and 3,3',5,5'-Tetra methyl benzidine Dihydrochloride.

21. The method according to claim 18, wherein the substrate is present in a volume of about 100 $\mu$L.

22. The method of claim 18, further comprising the step of reading a change of the color of the substrate with a colorimetric plate reader.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Hepatitis B virus

<400> SEQUENCE: 1
atactgcgga actcctagc                                              19

<210> SEQ ID NO 2
<211> LENGTH: 27
<212> TYPE: DNA
<213> ORGANISM: Hepatitis B virus

<400> SEQUENCE: 2
gttcacggtg gtctccatgc gacgtgc                                     27

<210> SEQ ID NO 3
<211> LENGTH: 22
<212> TYPE: DNA
<213> ORGANISM: Hepatitis B virus

<400> SEQUENCE: 3
gggcgcacct ctctttacgc gg                                          22